(12) United States Patent  (10) Patent No.: US 8,845,575 B2
Chewins et al.  (45) Date of Patent: Sep. 30, 2014

(54) WOUND TREATMENT APPARATUS

(75) Inventors: John George Chewins, Andover (GB); Allan Kenneth Frazer Grugon Hunt, Aldershot (GB)

(73) Assignee: Bioquell UK Limited, Hampshire (GB)

( * ) Notice: Subject to any disclaimer, the term of this patent is extended or adjusted under 35 U.S.C. 154(b) by 791 days.

(21) Appl. No.: 13/132,049

(22) PCT Filed: Mar. 8, 2010

(86) PCT No.: PCT/GB2010/000406
§ 371 (c)(1), (2), (4) Date: May 31, 2011

(87) PCT Pub. No.: WO2010/100439
PCT Pub. Date: Sep. 10, 2010

(65) Prior Publication Data
US 2011/0238004 A1   Sep. 29, 2011

(30) Foreign Application Priority Data

Mar. 6, 2009   (GB) .................................. 0903950.4

(51) Int. Cl.
| | |
|---|---|
| A61M 37/00 | (2006.01) |
| A61H 7/00 | (2006.01) |
| A61H 19/00 | (2006.01) |
| A61L 2/22 | (2006.01) |
| A61L 2/00 | (2006.01) |
| A61M 35/00 | (2006.01) |
| A61L 2/18 | (2006.01) |

(52) U.S. Cl.
CPC ........... *A61L 2/0088* (2013.01); *A61L 2202/16* (2013.01); *A61L 2/183* (2013.01); *A61L 2/22* (2013.01); *A61L 2202/13* (2013.01); *A61M 35/00* (2013.01)

USPC ............................................ 604/24; 601/166

(58) Field of Classification Search
CPC ............ A61M 1/0088; A61M 1/0058; A61M 1/0084; A61M 35/00; A61H 2033/143; A61H 2033/141; A61H 33/14
USPC ............... 604/290, 23, 24; 601/160, 166, 156
See application file for complete search history.

(56) References Cited

U.S. PATENT DOCUMENTS

| | | |
|---|---|---|
| 2008/0045874 A1 | 2/2008 | An |
| 2009/0020135 A1 | 1/2009 | Adams |

FOREIGN PATENT DOCUMENTS

| | | |
|---|---|---|
| DE | 298 18 910 | 4/1999 |
| WO | WO 2004/103452 | 12/2004 |

OTHER PUBLICATIONS

International Search Report & Written Opinon, Application No. PCT/GB2010/000406, May 31, 2010.

*Primary Examiner* — Aarti B Berdichevsky
*Assistant Examiner* — Bradley Osinski
(74) *Attorney, Agent, or Firm* — Workman Nydegger

(57) ABSTRACT

A wound treatment apparatus includes a tray (10) having a region adapted to receive a patient's body part (e.g. a leg) for treatment, a spray head (22, 23) for applying a spray of a gas containing liquid onto the body part and a covered well (13) in the tray having inlets (18) for surplus liquid and gas from the spray. Outlets are provided in communication with the well for gas and liquid respectively for connection to a suction to draw surplus liquid and gas from the well, and a unitary coupling (20) provides a plurality of fluid connections including a liquid supply for the spray head and liquid and gas withdrawal from said well outlets.

12 Claims, 12 Drawing Sheets

WOUND TREATMENT APPARATUS

BACKGROUND OF THE INVENTION

1. Field of the Invention

This invention relates to improvements in or relating to limb treatment apparatus and is intended to be used in conjunction with the apparatus for dispensing ozonated water or other gas containing liquids for treatment of body parts described and illustrated in our International Patent Application No. PCT/GB04/02212.

2. Present State of the Art

The latter application describes and illustrates apparatus for producing a spray of ozonated water for disinfecting a surface and in particular a skin area of a patient's limb comprising a vessel for water, a nozzle for spraying ozonated water onto a surface to be treated, an inner conduit for delivery of water from the vessel to the nozzle, means for supplying ozone to the water to be delivered as a spray of ozonated water from the nozzle and an outer conduit encircling the supply conduit having a shroud which encircles the nozzle to contain ozonated gas liberated at the nozzle wherein the nozzle has a number of orifices for delivering a spray of ozonated water and means are provided to create a negative pressure in the outer conduit to draw ozone liberated at the nozzle from the shroud into the outer conduit.

SUMMARY OF THE INVENTION

The primary object of the invention is to provide a tray connection system that:

(i) is designed to incorporate different tray designs (for use by patients with different types of wound);

(ii) allows for simultaneously delivery of aqueous ozone to the spray head, return of the waste aqueous ozone solution and return of any ozone gas released;

(iii) is designed to minimise ozone gas released from (a) the solution when it passes through the spray head and (b) from the solution as it moves through the tray;

(iv) is designed to support the application spray head and position it in relation to the support surface to be treated.

The apparatus of our prior International patent publication includes equipment which produces produce a high concentration aqueous ozone solution for delivery onto a wound via a low pressure multiple jet spray head. Gaseous phase ozone released in the spray process is captured as is waste solution which flows off the limb being treated.

An object of the present invention is to provide an apparatus for supporting a patient's limb for treatment having a spray head for a gas containing liquid with an arrangement for containing surplus liquid and gas from the treatment area.

This invention provides a wound treatment apparatus comprising a tray having a region adapted to receive a patient's body part for treatment, a spray head for applying a spray of a gas containing liquid onto the body part, a covered well in the tray having inlets for surplus liquid and gas from the spray, outlets in communication with the well for gas and liquid respectively for connection to suction means to draw surplus liquid and gas from the well, and a unitary coupling means for a plurality of fluid connections including a supply for the spray head and separate connections for passages from said well outlets for connection.

In one arrangement according to the invention the coupling means comprises a rotary coupling mounted on the tray and having an arm extending from the coupling over the tray on which the spray head is mounted for dispensing the spray onto the patient's body part.

More specifically the arm may be adjustably mounted on the coupling to enable, with the rotation of the coupling, the position of the spray to be adjusted to suit the location of the area on the patient's body part to be treated.

For example the connection between the coupling and spray head may comprise an inner conduit for delivering said liquid containing gas to the spray head from the coupling and an outer conduit encircling the inner conduit for connection to suction means for drawing gas released at the nozzle of the spray head back through the coupling.

The coupling may comprise a hollow chamber mounted for rotation about an axis of the chamber on the tray, the gas passage from the well and the outer conduit from the spray head being connected to the chamber for connection to suction means for drawing gas from the well and spray head and the chamber having two tube couplings, one leading to the nozzle of the spray head and the other leading from the outlet port for liquid from the well for connection to a supply of gas containing liquid and to pump means for withdrawing liquid from the well respectively.

In the latter arrangement the rotary coupling may comprise a two-part connector, one part mounted on the tray comprising said rotary housing to which the gas passage is connected and which contains the tube couplings for supplying and withdrawing liquid to the nozzle and well respectively and the other part of which comprises a cylindrical housing to mate with the housing on the tray connecting tube couplings for inter-engaging with the tube couplings in the tray mounted housing for supply and withdrawal of liquid respectively and having a connection for withdrawal of gas from the tray mounted housing and means being provided for locking the mating housings together.

In any of the above arrangements utilising a rotary housing on the tray, the housing may have a clamp in which the arm for supporting the nozzle is adjustably mounted in the radial direction with respect to the rotation of the mounting.

In any of the above arrangements the tray may be elongate and may have an upstanding end wall at one end of the tray in which said rotary housing is mounted for rotation about a horizontal axis with respect to the wall and the well comprises an elongate passage formed in the bottom of the tray extending lengthwise of the tray to the end wall and the rotary housing is mounted on the outside of the end wall for rotation about a horizontal axis extending over the tray, the outlet ports for gas and liquid respectively being formed at the end of the well adjacent the end wall and having passages leading from the ports up to the end wall to support means for coupling the passages to the interior of the rotary housing on the outside of the tray wall and the coupling for connection to pump means for withdrawing liquid from the well.

In any of the above arrangements, the spray shroud may be held in place by a clip designed to ensure that the spray shroud remains connected to the liquid delivery tube. The spray shroud may also have raised features on its surface to engage with a retaining clip, to allow the spray shroud to be mounted in a defined radial orientation and retaining the shroud in said required orientation. In any of the above arrangements, the spray shroud may possess surface markings to indicate the orientation and positioning of the spray shroud in relation to a wound.

In our International Patent Publication No. WO 2004/103452 an apparatus is described for disinfecting surface wounds using a high concentration aqueous ozone solution. Oxygen is critical to the wound healing process and a low pressure spray of water containing concentrated ozone enables a wound to be disinfected aiding the healing process. The apparatus for carrying out the treatment comprises three main components: an apparatus for generating a concentrated aqueous solution of ozone; an apparatus for spraying the ozone solution onto a surface of a limb to be treated; and an apparatus for supporting a limb to be treated and for collecting solution which flows off the treated limb for disposal. The latter apparatus comprises a catchment tray which includes a pump coupled to the tray for drawing off liquid received in the tray and delivering the liquid to a waste collection vessel.

BRIEF DESCRIPTION OF THE DRAWINGS

The present application relates to an improved form of catchment tray for a wound treatment apparatus and an embodiment of the tray will now be described with reference to the accompanying drawings in which.

DETAILED DESCRIPTION OF THE PREFERRED EMBODIMENTS

Figure 1:
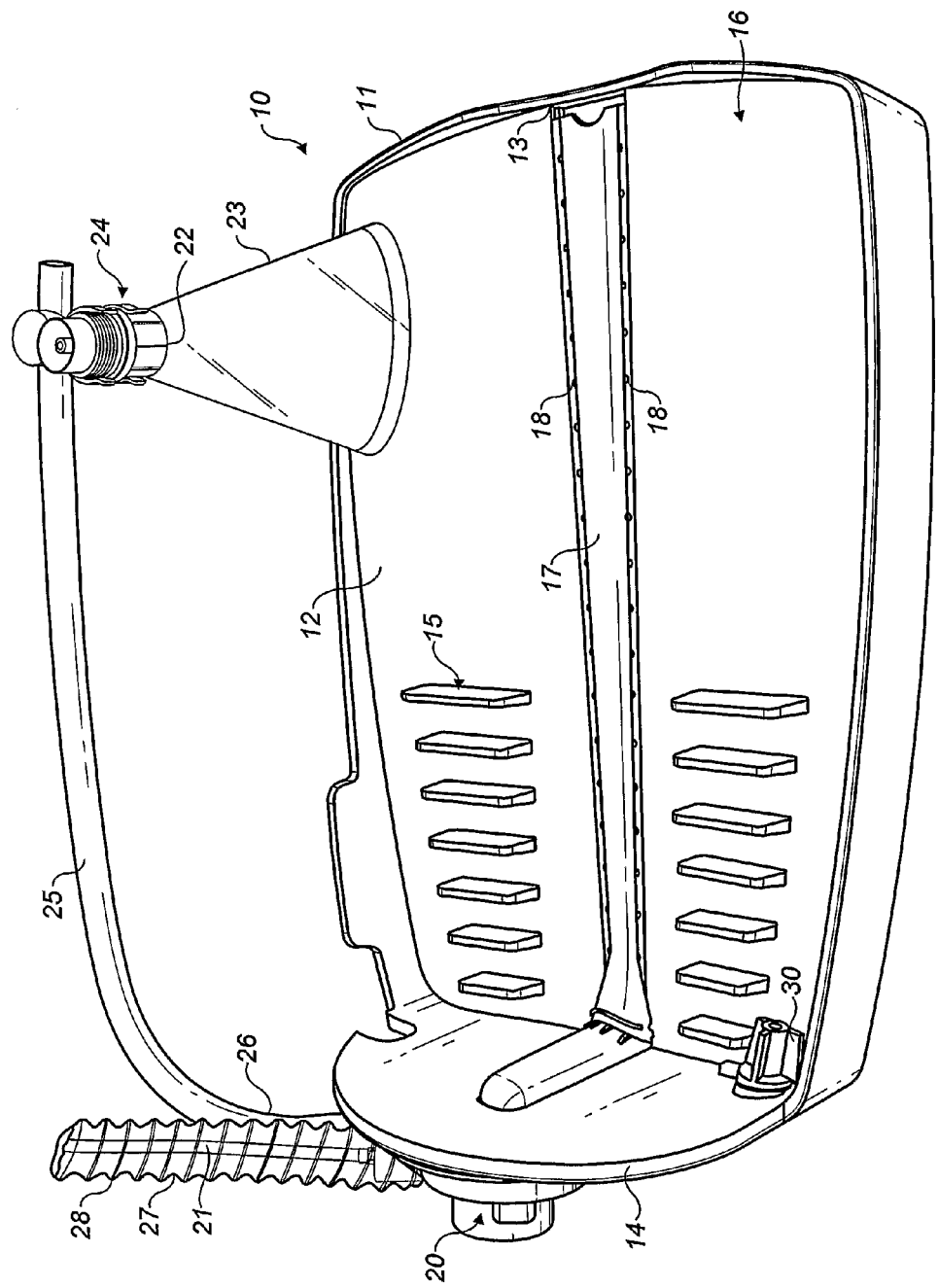
FIG. 1 is a perspective view of a catchment tray for a wound treatment apparatus including a spray head for delivery jets of a gas containing liquid onto an area of a patient's limb to be treated and a well in the tray for collecting surplus liquid/gas.

A catchment tray for a wound treatment apparatus using ozonated water is indicated generally at 10 and is of broadly rectangular form having an upstanding perimeter wall 11 and an inset base 12. The base has a central well 13 extending lengthwise of the base and the base slopes downwardly to the well from the perimeter wall on either side of the tray to promote flow of liquid into the well.

The tray has an upstanding end wall 14 at one end and the adjacent part of the base 12 is formed with spaced parallel upstanding ribs 15 to either side of the channel to accommodate a support cushion on which the patient's limb is rested for treatment. The ribs allow the cushion to be positioned in accordance with the size of the limb.

The well 13 at the centre of the base has a separate moulded cover plate 17 which extends substantially the full length of the well. The cover plate has multiple drain holes 18 spaced apart along the length of the cover adjacent its edges for drainage from the base 12 into the well.

A multi-passage quick action coupling indicated generally at 20 is mounted on the outside of the end wall 14 of the tray for rotation about a horizontal axis extending generally parallel to and above the centre line of the channel 13 in the tray. The coupling provides passageways for supply of ozonated water to the tray, for withdrawal of ozone gas released at the spray head or in the well of the tray and for withdrawal of spent water which accumulates in the well of the tray. The coupling has a radial outlet to which a flexible conduit 21 is connected for delivery of ozonated water from the coupling to a spray head 22 mounted in a transparent funnel shaped shroud 23.

The shroud nozzle, coupling to the shroud and mounting of the shroud are shown in greater detail in FIGS. 15 to 18 and will be described later. The shroud is mounted by a moveable clamp 24 to a bar 25 extending over the tray. The bar has a radial arm 26 (with respect to said horizontal axis) at the end adjacent the end wall of the tray which is mounted in a releasable clamp on the rotary part of the coupling 20 to enable the radial position of the bar 25 with respect to the tray to be adjusted. The coupling allows the bar 25 to be positioned over the tray to provide the required discharge angle and spacing from the area of the patient's limb to be treated.

The flexible conduit 21 for delivering ozonated water from the coupling to the spray head 22 is enclosed in an encircling flexible plastic sleeve 27 supported by a spirally wound wire 28 to provide a co-axial passage around the conduit 21 between the coupling and spray head around the conduit. The passage is connected at one end through the coupling 20 to a source of vacuum and is in communication at the other end with the space around the spray head in the shroud 23 so that ozone released from the jets of ozonated water discharged from the nozzle of the spray head is drawn back into the passage and is not released to atmosphere. The conduit 21/outer sleeve 27 are connected to the sprayhead/shroud through a co-axial coupling 29 which can be inserted and withdrawn from the shroud as required.

Figure 2:
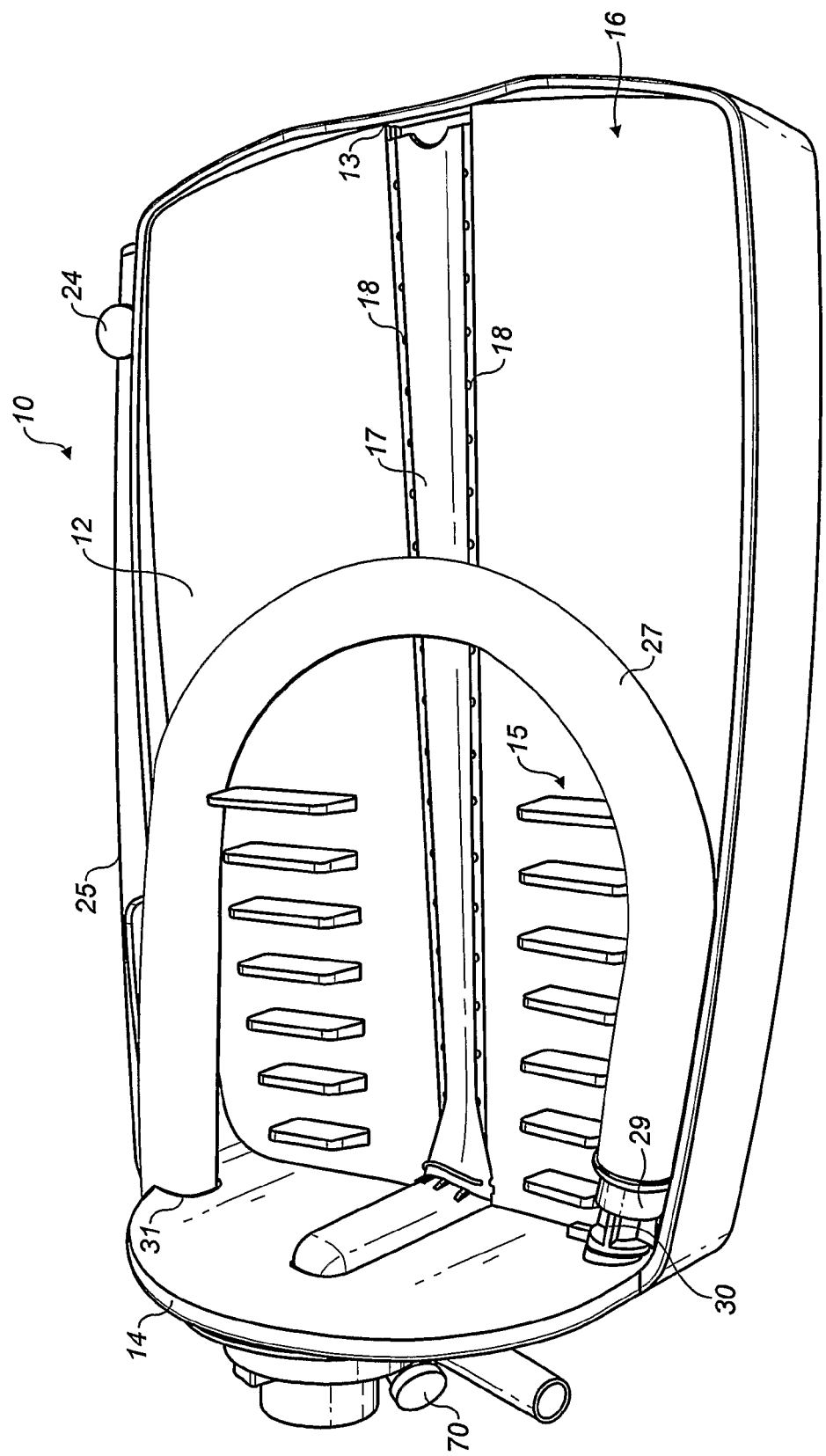
FIG. 2 is a similar view to FIG. 1 showing the spray head, its mounting and supply conduit in stowed positions on the tray.
Figure 3:
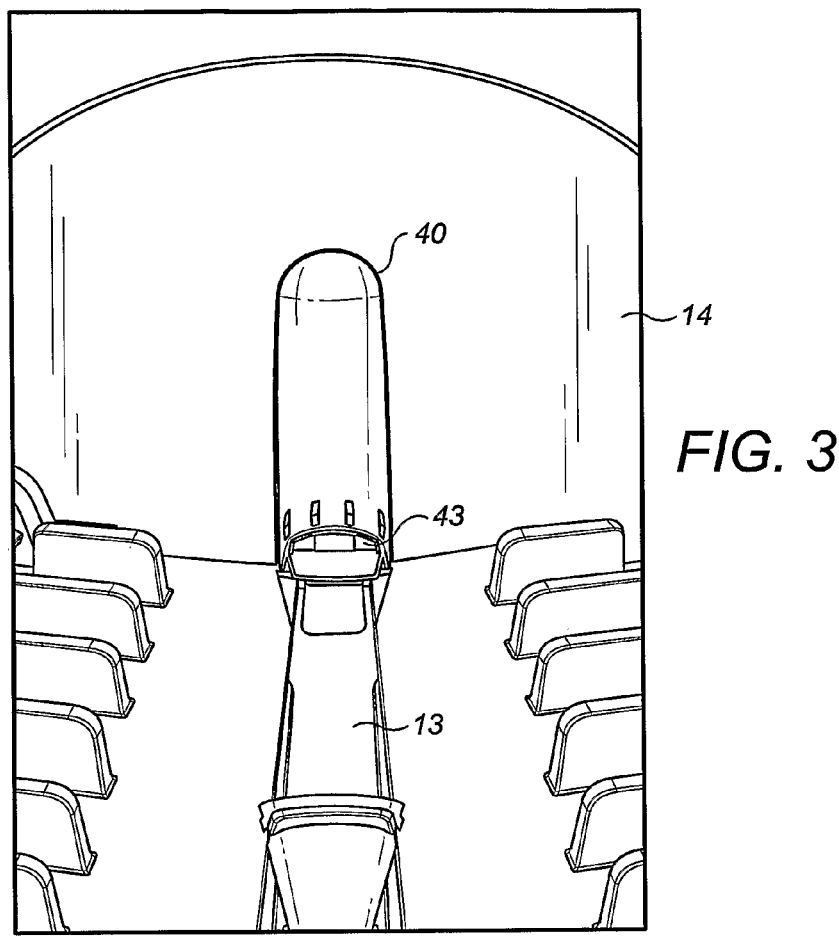
FIG. 3 shows the base of the tray and adjacent end wall with the cover for the well retracted to reveal the arrangement for separating liquid and gas flows from the well in the tray into the cover.
Figure 4:
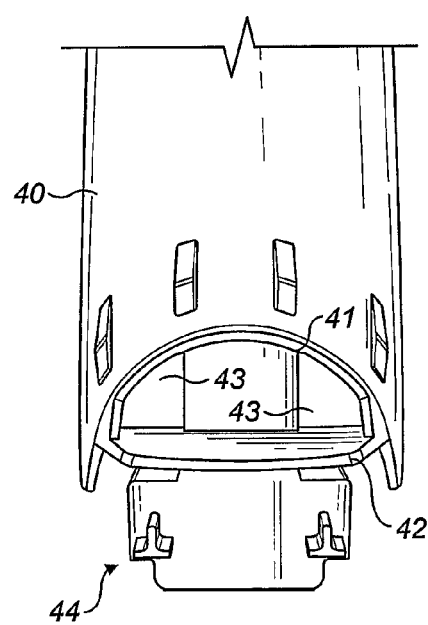
FIG. 4 shows the lower end of the cover for the vertical channel.

FIG. 2 shows the tray of FIG. 1 with the bar 25 and clamp 24 stowed out of use and the spray head/shroud removed. The conduit 21/sleeve assembly 27 are laid in the tray with the co-axial coupling 29 engaged on a plug 30 on the inside of the end wall 14 in one corner of the tray to hold the conduit in place. The end wall in the opposite corner of the tray has a cut-out 31 for the conduit/sleeve to extend through into the tray.

Referring now to FIGS. 3 to 6 of the drawings, the cover 17 for the well is shown withdrawn from the end of the well adjacent the end wall of the tray. The end wall 14 is formed with an upwardly extending shallow channel 35 leading from the well to an insert plate 36 mounted in the end wall having a central port 37 and outer arcuate ports 38 which are co-axial with the coupling 20 on the outside of the end wall. The channel has a cover 40 the lower end of which is shown in detail in FIG. 4 and includes an opening indicated generally at 41 into the end of the cover. The opening 41 is divided horizontally by a plate 42 to provide an upper inlet port 43 for gas flow into the cover and a lower inlet indicated at 44 for liquid flow.

Figure 5:
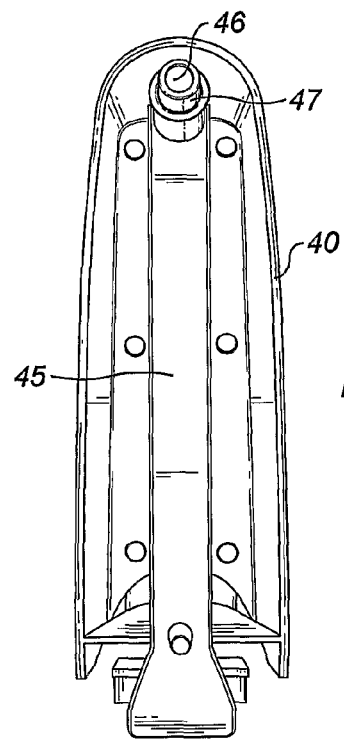
FIG. 5 is a perspective view of the reverse side of the cover.
Figure 6:
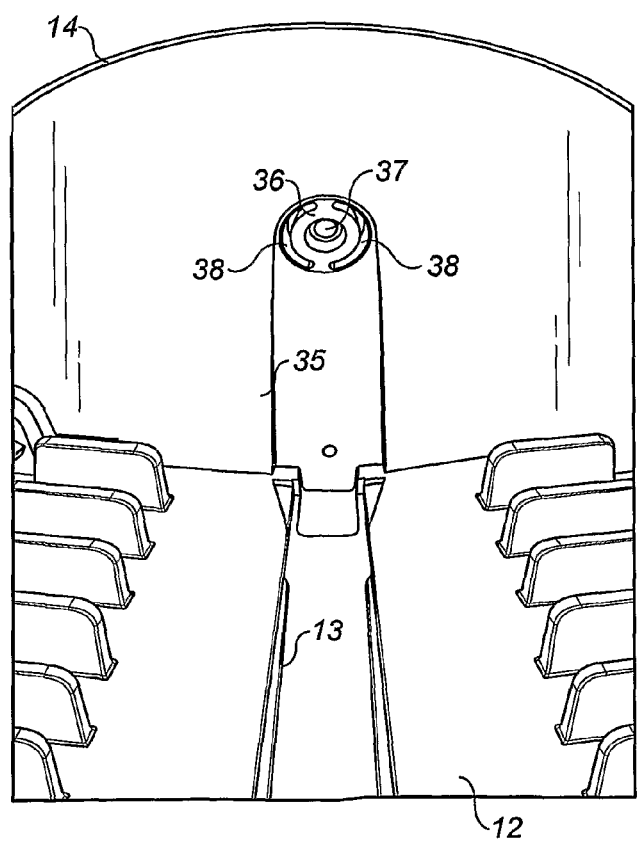
FIG. 6 shows the well in the base of the tray and the channel in the end wall both with covers removed.
Figure 7:
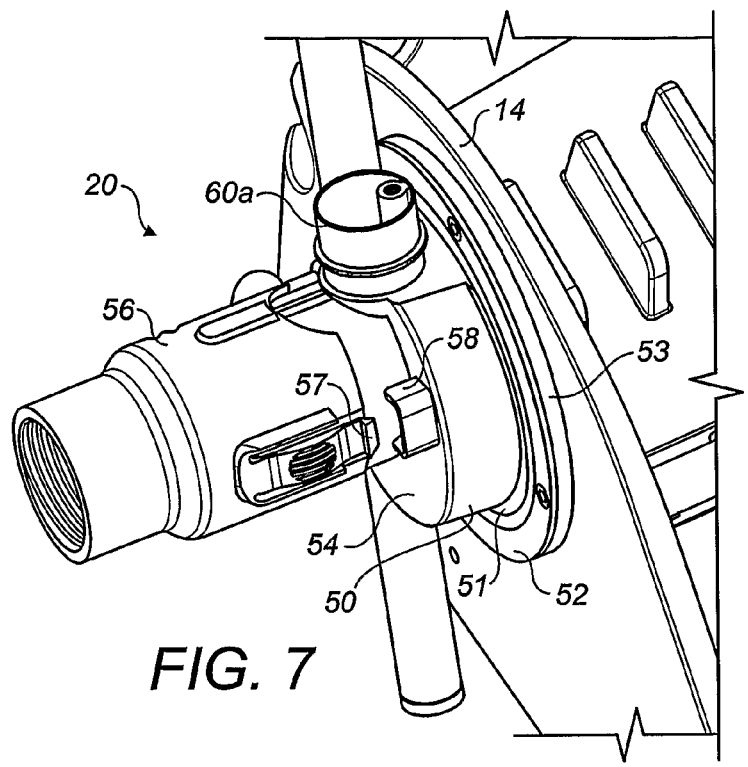
FIG. 7 is a perspective view of the outside of the end wall of the tray showing a plug and socket connection rotatably mounted on the end wall of the housing for supporting the spray head and for connecting a supply of gas containing liquid to the spray head and for withdrawing surplus gas and liquid, the socket being partially engaged with the plug.
Figure 8:
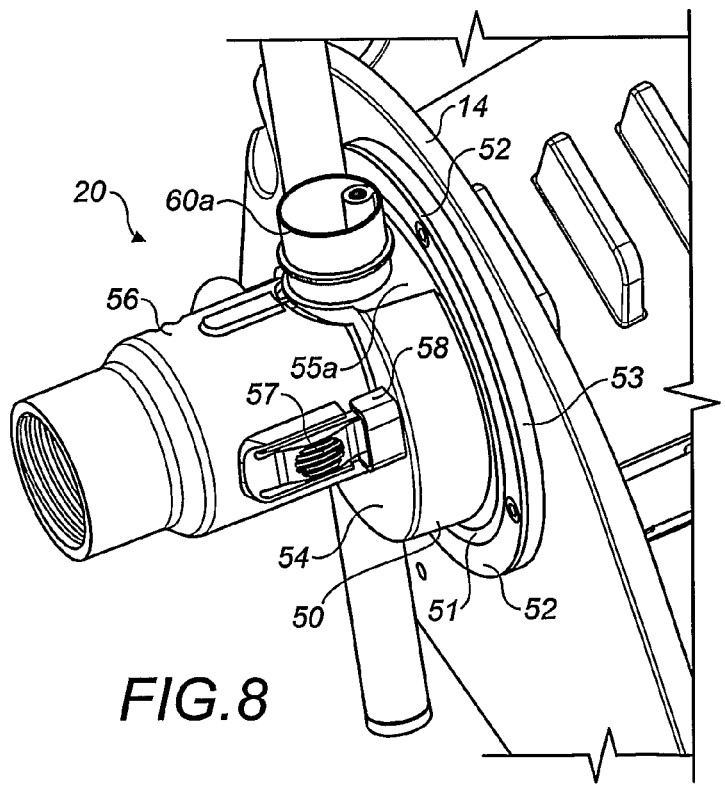
FIG. 8 is a similar view to FIG. 7 showing the socket fully engaged with the plug.

Referring to FIG. 5 of the drawings which shows the reverse side of the cover, a conduit 45 extends from the inlet 44 to the upper end of the cover where the conduit connects to an integral horizontal tube 46 to engage in the central port 37 in plate 36. The interior of the cover around the conduit 45 provides a passageway for gas entering the cover through the port 43. The upper end of the passageway in the cover leads to the arcuate ports 38 in plate 36.

As described later, the port 37 is connected through the multi-passage coupling to a pump for drawing off liquid accumulating in the well 13 of the catchment tray via the passage 45 and tube 46. A fan is provided for drawing off ozone gas accumulating in the tray which is drawn through the port 43 at the bottom of the cover into the passage extending up the cover to the arcuate ports 38 where it is drawn out through the coupling.

Reference is now made to FIGS. 7 to 10 of the drawings which show the multi passage separable coupling 20 and its rotary mounting on the outer side of the end wall 14 of the tray. The multi-passage rotary coupling comprises a generally annular housing 50 having an integral out-turned stepped peripheral flange 51 on one side which is located within an annular upstanding rib formed integrally on the end wall of the tray coaxially with the port 37. An annular plate 52 is secured to the rib and overlies a step 53 in the out-turned flange of the housing to hold the housing on the end wall of the tray whilst allowing the housing to rotate about an axis defined by the port 37.

The other end of the housing has an integral end wall 54 on which an annular hub 55 is integrally formed extending through the end wall. The hub is offset from the axis of the housing towards one side of the housing where there is a flat face 55*a* formed in the annular wall of the housing for a purpose which will be described later.

A cap 56 is releasably connected to the hub by means of detent legs 57 formed integrally on the cap which engage in sockets 58 formed integrally with the end wall 54 of the housing on either side of the hub.

An extension sleeve 59 is mounted at one end in the port 37 in the end wall and projects into the annular hub 55. A male component 60 of a two-part push-in fluid coupling of the type described and illustrated in US Patent Publication No. 2007/0025811 of Colder Products Company is mounted in one end of the sleeve 59. The female part 61 of the fluid coupling is mounted in the cap 56 on a cross member 62 located in the cap. The female part of the coupling is opened automatically by insertion of the male component to allow fluid to flow through the coupling. The female part of the coupling is connected by a further conduit 63 to a pump (not shown) to withdraw waste fluid from the well of the tray up through the cover to the port 37, through the connection sleeve and the two-part coupling.

A second two-part push-in fluid coupling is located in the cap to one side of the coupling 60,61. The second coupling has a male part 65 mounted in the annular hub 50 and connected to an out-turned elbow connector 66. The elbow connector has a radially extending conduit 67 which extends through face 55*a* of the hub 50 and to which the tube 21 for delivering ozonated water to the spray head is coupled by a screw-in connector 68. The second fluid coupling has a female part 69 mounted in the cap and connected to a supply of ozonated water via a pump connection 70 and conduit.

The conduit 67 is formed within a stub pipe 71 formed integrally with the flat face 55*a* on the outer wall of the housing. The stub pipe receives an end of the sleeve 28 which encircles the supply conduit 21 for delivering fresh ozonated water to the nozzle. The sleeve 28 which encircles the supply conduit 21 is connected to the stub pipe by a clamp (not shown).

The cap 56 is connected by a flexible pipe to an evacuating pump. Thus gas is drawn from the space around the nozzle from which ozonated water is sprayed so that ozone gas released at the nozzle is drawn back through the sleeve 27, the stub pipe on the housing and into the housing and then through the cap to be disposed. In addition to the gas drawn from the nozzle through the sleeve 27, waste gas liberated in the wound area is drawn into the well via the openings 80 in the cover 17 and thence is drawn upwardly through the channel to the arcuate slots around the aperture 37 from where the gas passes into the boss of the hub and thence through the cap from where it is drawn away by the pump referred to earlier.

Figure 14:
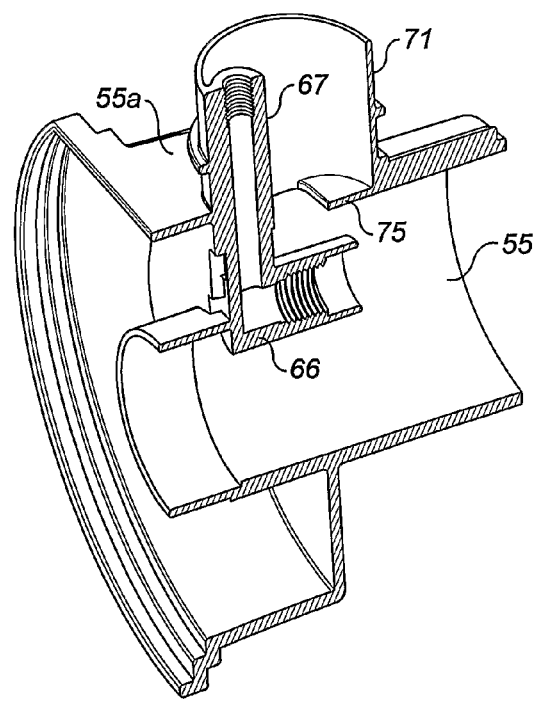
Figure 15:
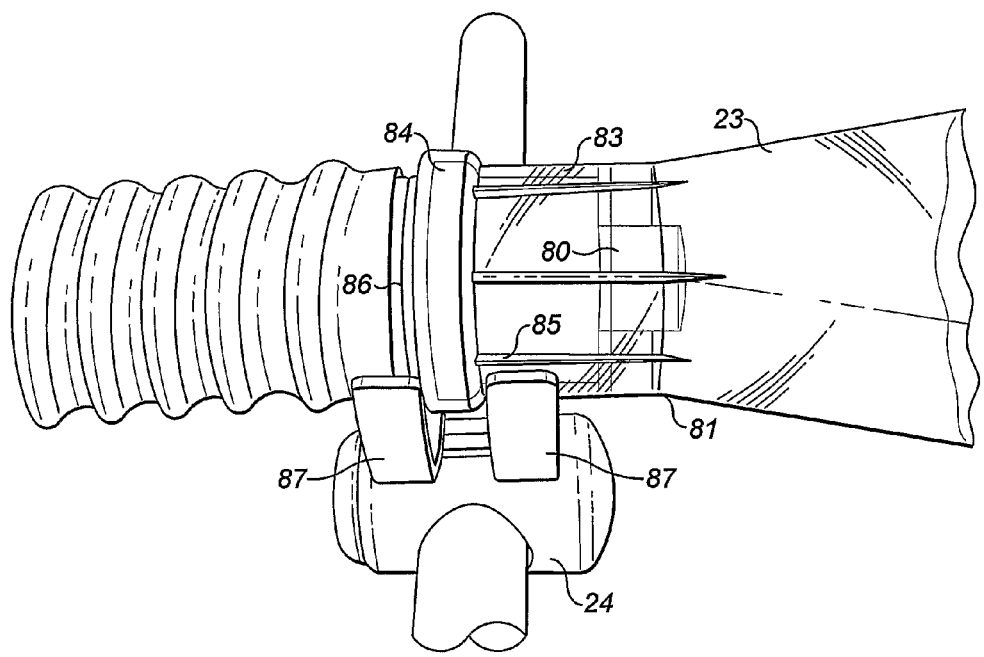
FIGS. 15 and 16 show the mounting of a shroud of the spray head on the tray.
Figure 16:
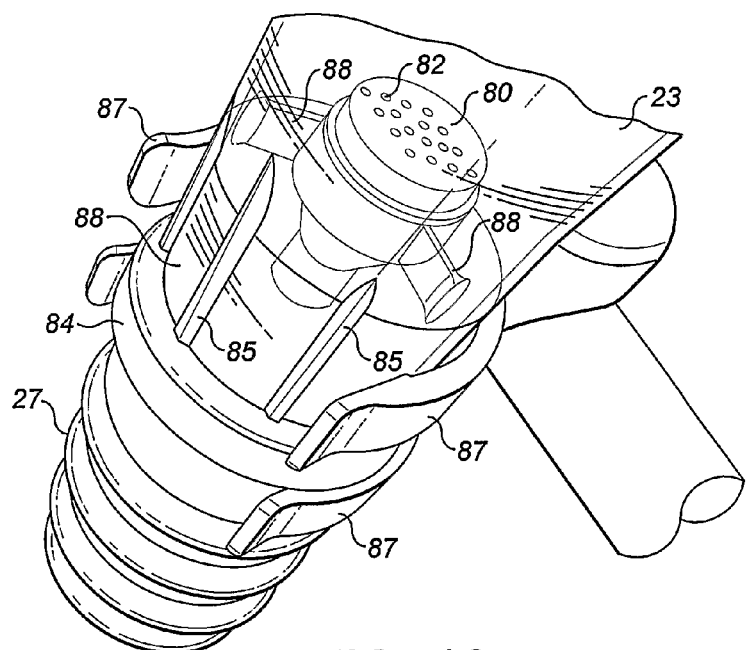
Figure 17:
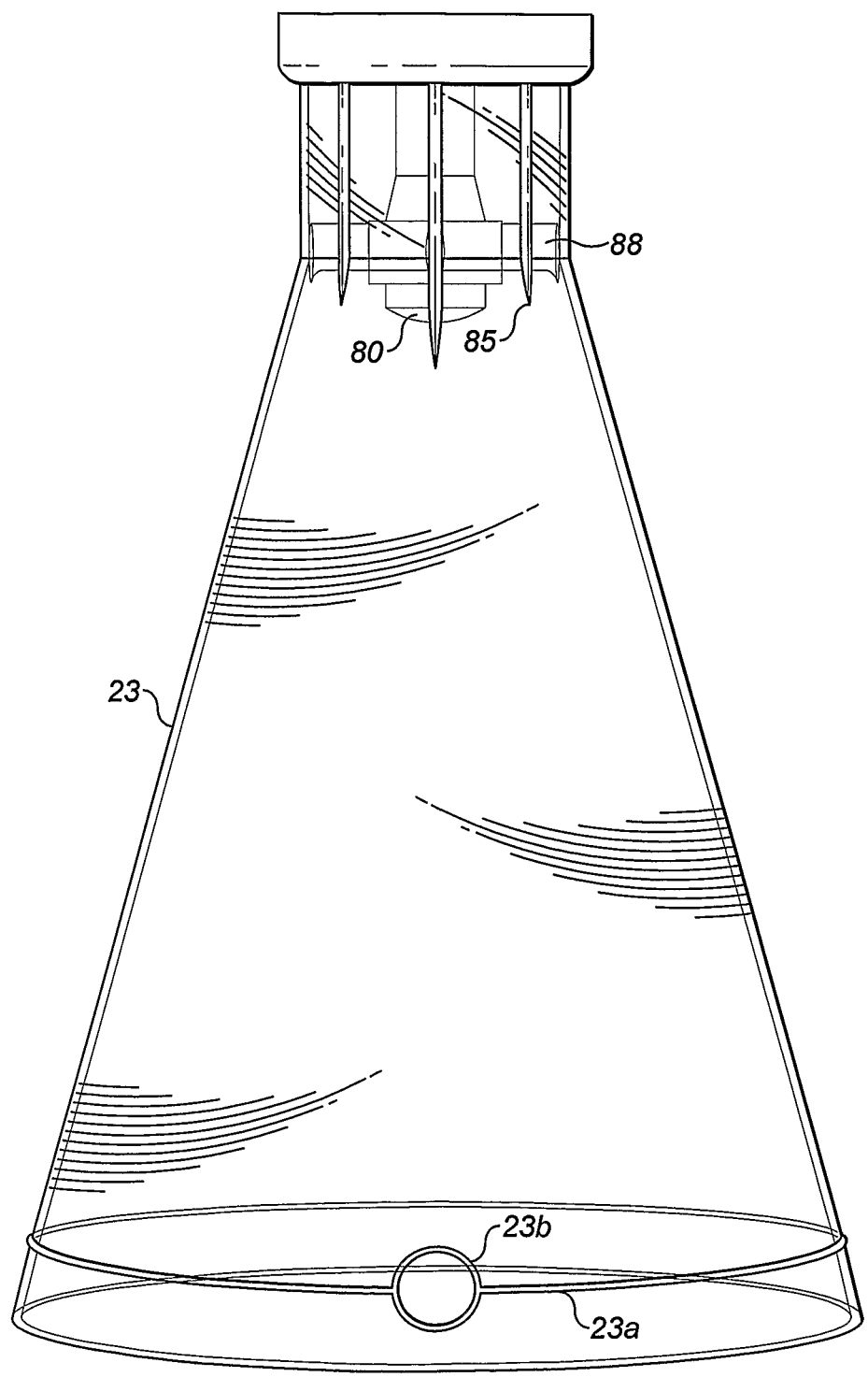
FIGS. 17 and 18 show the shroud in greater detail.

The space in the cap around the couplings 60,61 and 65 and 69 which is indicated at 72 communicates with the interior of the hub 55 and is connected to a suction pump via a gas line (not shown) for drawing off ozone gas from the spray head and the catchment tray for delivery to a catalyst for breaking down the ozone into oxygen for release to atmosphere as described in our International Patent Application No. WO 2004/103452. FIG. 14 shows the space in the coupling which contains a baffle 75 to control the partitioning of the air flow from the spray head and tray.

Figure 9:
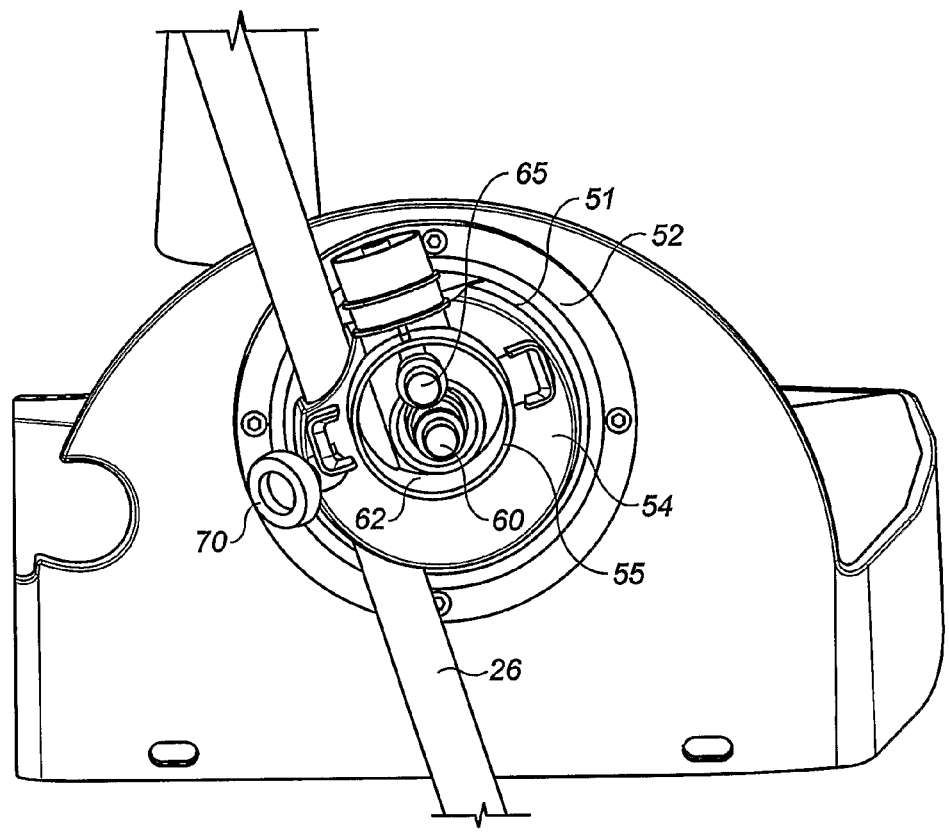
FIG. 9 is an end view of the socket showing the separate supply connections for gas containing liquid and for withdrawing surplus liquid and surplus gas.
Figure 10:
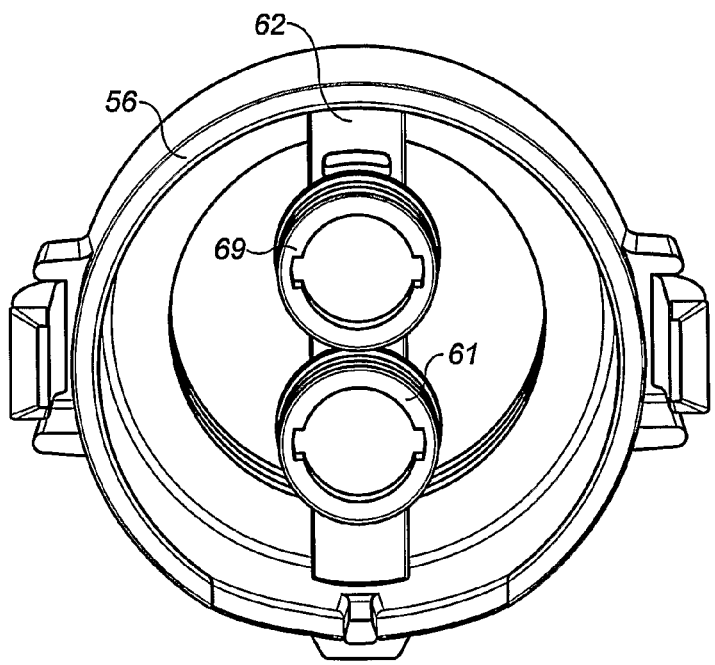
FIG. 10 is an end view of the plug for engaging in the socket.
Figure 11:
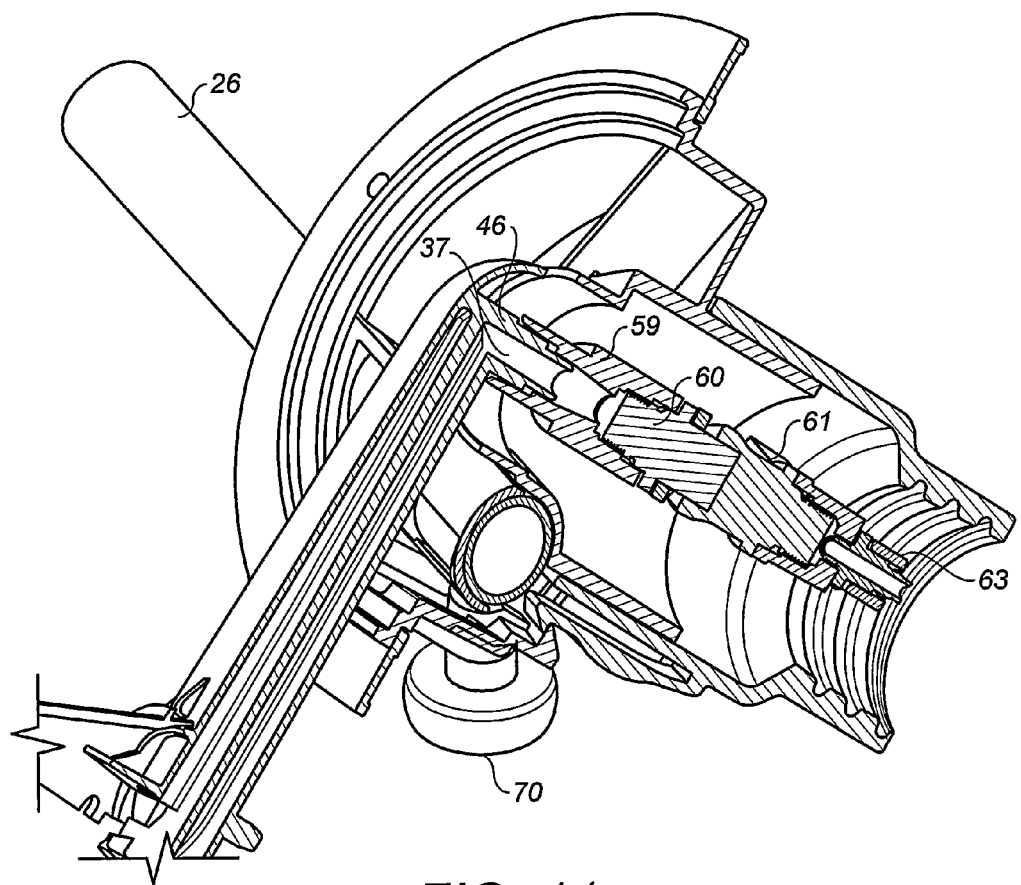
FIGS. 11 to 14 show various scrap sectional views of the arrangement on the tray for delivery of gas carrying liquid and recovery of surplus gas and liquid.
Figure 12:
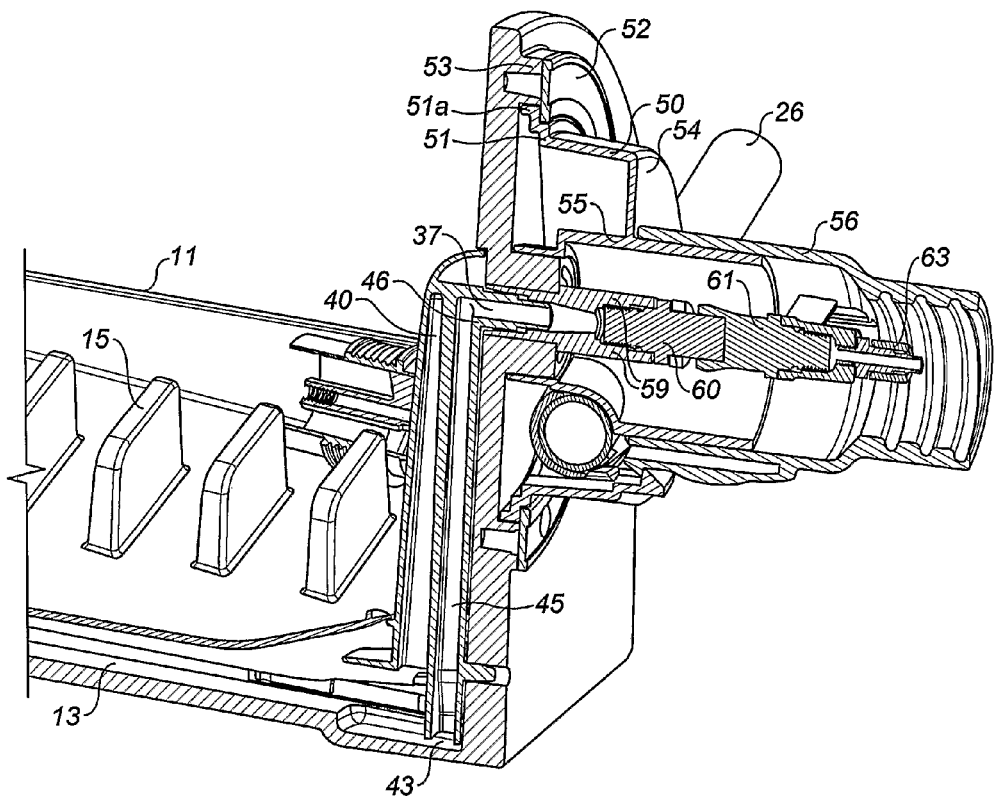
Figure 13:
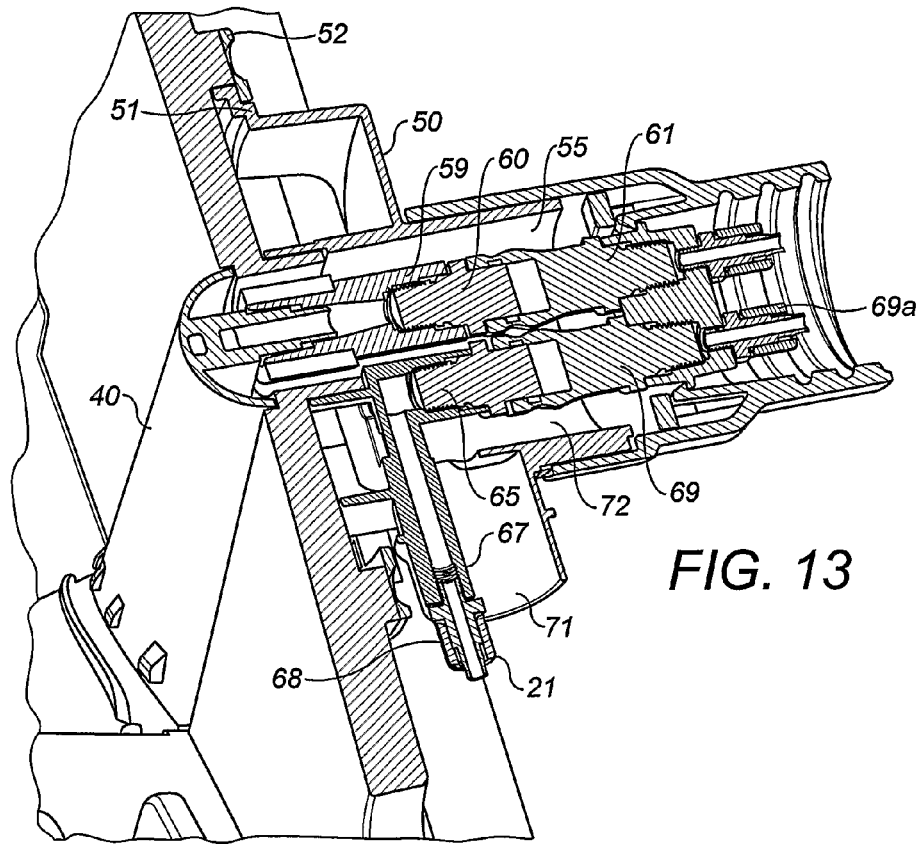

The bar 25 which carries the spray head has an in-turned arm 26 at one end which is mounted in a clamp arrangement indicated at 70 on FIG. 9 of the drawings. The clamp is releasable to allow the position of the arm in the clamp to be adjusted and thereby adjust the radial position of the bar 25 with respect to the catchment tray as described earlier.

Reference is now made to FIGS. 15 to 18 of the drawings which show the spray shroud 23 and its mounting and coupling to the supply of ozonated water and extraction of gas from the shroud in greater detail. It will be seen that the shroud has a tapered shallow oval cross-section and the spray head 22 located at the apex 81 of the shroud has a corresponding arrangement of jets 82 aligned with the shroud to generate a stream of generally oval cross-section to be directed at a patient's wound. The shroud has an integral conduit 83 at its apex which terminates in an annular head 84 at the end of the sleeve. The conduit 83 has spaced longitudinally extending ribs 85 at spaced locations around its outer periphery.

The conduit 21 and encircling sleeve 27 are secured to a co-axial tubular connector 86 located in the conduit 83 of the shroud. The shroud/conduit assembly is mounted on the clamp 24 on the spray bar by dual C-shaped clips 87 which snap over the conduit 83 and connector 27 to hold the connector in the conduit and to support the shroud on the clamp. The arms of the C-shaped clips have upstanding ribs 87 towards the mouth of each clip so that the ribs of the clip provide, with the ribs 85 on the conduit 83, an indexing arrangement for controlling the rotation or position of the shroud with respect to the clamp 24.

Figure 18:
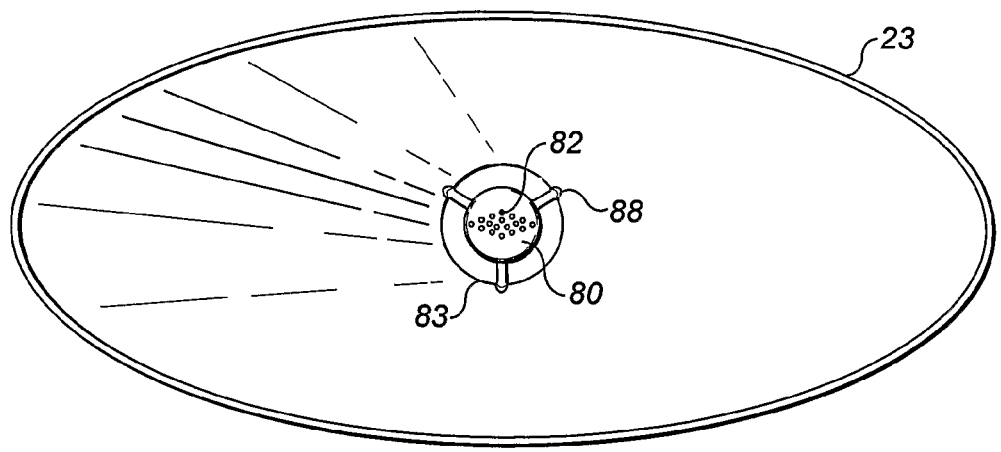

FIG. 18 is a view looking into the shroud and illustrates the nozzle 80 mounted on three equi-spaced legs 88 in the apex of the shroud with jets in the nozzle for creating a spray pattern corresponding to the general oval shape of the nozzle as described earlier.

The spray shroud has an encircling line 23*a* spaced from the mouth of the shroud by a distance corresponding to the distance the shroud should be positioned from a surface to optimise removal of ozone gas by the shroud 23. The line 23*a* has a ring 23*b* on one side of the shroud which indicates the surface which should be uppermost to maximize ozonated fluid lavage through the wound. The shroud 23 is designed to deliver a greater volume of water to the upper surface of a wound to increase a lavage effect.

The apparatus is used for dealing with ulcers and other wounds on a patient's skin as described in our previous International application to which reference should be made. The apparatus has a computer control system for controlling the various functions of the apparatus again as described previously.

The arrangement provides a catchment tray having a multi-conduit quick-connect coupling system for simultaneously delivering an off gassing, decontaminating solution such as aqueous ozone to the spray head along with the return of any waste solution the diversion of any unwanted off gas to a catalyst destruction circuit. More particularly, the coupling system comprises a multi port, multi phase conduit quick-connect coupling with control and optimisation of flow rates to achieve a safe, effective, reliable connection system for delivering an off gassing decontaminating solution from a producing unit to the spray head. Thus the problem solved by the invention is the provision of a safe, easy-to-use (the tray is to be connected to a main unit each time a patient is treated by a nurse), universal (connector capable of being used with different tray designs) tray connection system. The apparatus is designed in particular to spray aqueous ozone onto a wound surface at a predetermined concentration and rate, whilst actively removing ozone gas released by the application of the solution through the wound surface. The device incorporates a method of collecting the solution after it has been applied. The aqueous ozone solution used disinfects the wound surfaces and promotes healing within the wounds.

The connection system minimises release of ozone gas when the apparatus is used by patients either positioned on a bed or in a wheelchair.

The invention claimed is:

1. A wound treatment apparatus comprising:

a tray having a region adapted to receive a patient's body part for treatment, a spray head for applying a spray of a gas containing liquid onto the body part, a covered well in the tray having inlets for surplus liquid and gas from the spray, outlets in communication with the well for gas and liquid respectively for connection to suction means to draw surplus liquid and gas from the well, and a unitary coupling means for a plurality of fluid connections including a liquid supply for the spray head and liquid and gas withdrawal from said well outlets.

2. A wound treatment apparatus as claimed in claim 1, wherein the unitary coupling means is rotatably mounted on the tray for rotation about an axis extending generally parallel to and above the tray and the coupling further includes an arm extending from the coupling over the tray on which the spray head is mounted for rotation with the coupling to adjust the direction of the spray from the spray head.

3. A wound treatment apparatus as claimed in claim 2 wherein the spray head is mounted within a moveable clip and has surface features which interact with the clip to secure the shroud to the liquid delivery pipe and hold the shrouds orientation.

4. A wound treatment apparatus as claimed in claim 2, wherein the arm is adjustably mounted on the coupling means for adjustment of the arm radially of the coupling axis to enable, with the rotation of the coupling, the position of the spray to be adjusted to suit the location of the area on the patient's body part to be treated.

5. A wound treatment apparatus as claimed in claim 4, wherein the connection between the coupling and spray head comprises an inner conduit for delivering said liquid containing gas to the spray head from the coupling and an outer conduit encircling the inner conduit for connection to suction means for drawing gas released at the nozzle of the spray head back through the coupling.

6. A wound treatment apparatus as claimed in claim 5, wherein the coupling comprises a hollow chamber mounted for rotation about an axis of the chamber on the tray, the gas passage from the well and the outer conduit from the spray head being connected to the chamber for connection to suction means for drawing gas from the well and spray head and the chamber having two tube couplings, one leading to the nozzle of the spray head and the other leading from the outlet port for liquid from the well for connection to a supply of gas containing liquid and to pump means for withdrawing liquid and gas from the well respectively.

7. A wound treatment apparatus as claimed in claim 6, wherein the rotary coupling comprises a two-part connector, one part mounted on the tray comprising said rotary housing to which the gas passage is connected and which contains the tube couplings for supplying and withdrawing liquid to the nozzle and well respectively and the other part of which comprises a cylindrical housing to mate with the housing on the tray connecting tube couplings for inter-engaging with the tube couplings in the tray mounted housing for supply and withdrawal of liquid respectively and having a connection for withdrawal of gas from the tray mounted housing and means being provided for locking the mating housings together.

8. A wound treatment apparatus as claimed in claim 7, wherein the rotary housing on the tray has a clamp in which the arm for supporting the nozzle is adjustably mounted in the radial direction with respect to the rotation of the mounting.

9. A wound treatment apparatus as claimed in claim 6, wherein the rotary housing on the tray has a clamp in which the arm for supporting the nozzle is adjustably mounted in the radial direction with respect to the rotation of the mounting.

10. A wound treatment apparatus as claimed in claim 5, wherein the rotary housing on the tray has a clamp in which the arm for supporting the nozzle is adjustably mounted in the radial direction with respect to the rotation of the mounting.

11. A wound treatment apparatus as claimed in claim 1, wherein the tray is elongate and has an upstanding end wall at one end of the tray in which said rotary housing is mounted for rotation about a horizontal axis with respect to the wall and the well comprises an elongate passage formed in the bottom of the tray extending lengthwise of the tray to the end wall and the rotary housing is mounted on the outside of the end wall for rotation about a horizontal axis extending over the tray, the outlet ports for gas and liquid respectively being formed at the end of the well adjacent the end wall and having passages leading from the ports up to the end wall to support means for coupling the passages to the interior of the rotary housing on the outside of the tray wall and the coupling for connection to pump means for withdrawing liquid from the well.

12. A wound treatment apparatus as claimed in claim 1 wherein the spray shroud has surface features which show the positioning and orientation of the spray shroud in relation to the surface to be treated.

* * * * *